United States Patent [19]

Herzenberg et al.

[11] Patent Number: 5,580,577
[45] Date of Patent: Dec. 3, 1996

[54] METHOD OF TREATING THE SYMPTOMS OF HUMAN RHINOVIRUS INFECTION

[76] Inventors: Leonard A. Herzenberg; Leonore A. Herzenberg, both of 876 Cedro Way, Stanford, Calif. 94305

[21] Appl. No.: 544,363

[22] Filed: Oct. 17, 1995

Related U.S. Application Data

[63] Continuation of Ser. No. 159,945, Nov. 29, 1993, abandoned, which is a continuation of Ser. No. 34,641, Mar. 22, 1993, abandoned, which is a continuation of Ser. No. 832,606, Feb. 12, 1992, abandoned, which is a continuation-in-part of Ser. No. 463,618, Jan. 11, 1990, abandoned.

[51] Int. Cl.$^6$ .............................. A61K 9/08; A61K 9/20; A61K 9/48
[52] U.S. Cl. .................. 424/451; 424/464; 514/562; 514/563; 514/885; 560/16; 562/557
[58] Field of Search ...................... 424/451, 400, 424/464; 514/562, 563, 885–888; 560/16; 562/557

[56] References Cited

U.S. PATENT DOCUMENTS

| | | | |
|---|---|---|---|
| 3,184,505 | 5/1965 | Martin et al. | 562/557 |
| 4,184,885 | 4/1979 | Renoux et al. | 424/163 |
| 4,335,210 | 6/1982 | Meister et al. | |
| 4,434,158 | 2/1984 | Meister et al. | |
| 4,438,124 | 3/1984 | Meister et al. | |
| 4,440,788 | 4/1984 | Terayama et al. | 514/893 |
| 4,619,934 | 10/1986 | Sunshine et al. | 514/277 |
| 4,647,571 | 3/1987 | Meister et al. | |
| 4,665,082 | 5/1987 | Meister et al. | |
| 4,708,965 | 11/1987 | Morgan | 514/563 |
| 4,710,489 | 12/1987 | Meister | |
| 4,724,232 | 2/1988 | Rideout et al. | |
| 4,744,989 | 5/1988 | Payne et al. | |
| 4,758,551 | 7/1988 | Meister et al. | |
| 4,772,471 | 9/1988 | VanLerberghe et al. | |
| 4,784,685 | 11/1988 | Meister | |
| 4,789,633 | 12/1988 | Huang et al. | |
| 4,827,016 | 5/1989 | Morgan | 560/16 |
| 4,879,370 | 11/1989 | Meister | |
| 4,931,473 | 6/1990 | Kellener et al. | 514/688 |
| 4,968,506 | 11/1990 | Appelgren et al. | 424/456 |
| 4,970,236 | 11/1990 | Ziggiotti et al. | 514/562 |
| 4,985,241 | 1/1991 | Zimmerman et al. | 424/85.1 |
| 5,080,906 | 1/1992 | Carenzi et al. | 424/452 |

FOREIGN PATENT DOCUMENTS

| | | |
|---|---|---|
| 0158487 | 3/1985 | European Pat. Off. |
| 3812008 | 4/1988 | Germany |
| 3707127 | 9/1988 | Germany |
| WO88/09674 | 12/1988 | WIPO |

OTHER PUBLICATIONS

Passwater, *Super Nutrition*, Gulfwestern Pocket Books, NY, NY, pp. 154, 155, (1976).

Burton et al, *Human Nutrition*, 4th ed. McGraw–Hill, pp. 50–53, 60–62, (1988).

West et al, *Textbook of Biochemistry*, 4th ed. Macmillan, NY, NY, pp. 1143–1147 and 1243–1250.

"Surrogate Endpoints in Evaluating the Effectiveness of Drugs Against HIV Infection and AIDS", Sep. 11–12, 1989, Conference Summary, Robin Weiss and Leah Mazade, editors, The Roundtable for the Development of Drugs and Vaccines Against AIDS, Institute of Medicine, National Academy Press, Washington, DC, 1990.

Ishii et al, *Journal of Cellular Physiology*, 133:330–336 (1987).

Kosower et al, *Nature*, 224:117–120 (1969).

Ketterer, *Mutation Research*, 202:343–361 (1988).

Ziegler, *Ann. Rev. Biochem.*, 54:305–29 (1985).

Orrenius et al, "Regulation of Calcium Compartmentation in the Hepatocyte—A Critical Role of Glutathione", *Functions of Glutathione: Biochemical Physiologicl, Toxicological, and Clinical Aspects*, Larsson et al eds., Raven Press, NY NY, 1983, pp. 261–271.

Martensson et al, *Proc. Natl. Acad. Sci. USA*, 86:471–475 (1989).

Droge et al, *Immunobiol.*, 172:151–156 (1986).

Ristow et al, *Immunological Investigations*, 14:(5)401–414 (1985).

Bannai et al, *J. Membrane Biol.*, 89:1–8 (1986).

Wu et al, *Clin. exp. Immunol.*, 77:7–10 (1989).

Richman et al, *The American Journal of Medicine*, 85:208–213 (Suppl 2A) (1988).

Moldeus et al, *Respiration*, 50: Suppl. 1, 31–42 (1986).

Ziment, *Respiration*, 50: Suppl. 1, 26–30 (1986).

Yunis et al, *Respiration*, 50: Suppl. 1, 50–55 (1986).

de Quay et al, "Glutathione Depletion in HIV–infected Patients: Role of Cysteine Deficiency and Effect of Oral N–Acetylcysteine", Swiss National Foundation for Scientific Research.

Mitsuya et al, *Japan Sci. Soc. Press Utrect*, pp. 277–288, (1985).

Moody et al, "Potential therapeutic application autologous CD8+ cells from HIV–infected subjects." IV Int. Conf. AIDS (abstract) Stockholm (1988).

Droge et al, *Biol. Chem. Hoppe–Seyler*, 369:143–148, (1988).

(List continued on next page.)

Primary Examiner—John C. Bleutge
Assistant Examiner—Robert H. Harrison

[57] ABSTRACT

A method of treating viral infection comprises the step of administering to a patient harboring a disease-inducing virus other than HIV-1, the virus being one for which an intracellular thiol deficit causes or exacerbates expression of viral genetic information by transcription, translation or viral replication, such as human rhinovirus, an amount effective to inhibit transcriptional or translational expression of genetic information or replication of the virus, of an N-($C_{1-4}$)-acylcysteine, such as N-acetyl cysteine, or a pharmaceutically acceptable salt thereof. Prevention of disease symptoms and reduction of their severity results from the foregoing treatment. Combination of N-($C_{1-4}$)-acylcysteine or its salt with another antiviral drug or drug for alleviating symptoms of viral infection provides additional therapeutic benefits.

2 Claims, No Drawings

OTHER PUBLICATIONS

Eck et al, *Biol. Chem. Hoppe-Seyler,* 370:109–113, (1989).

Eck et al, *Biol. Chem. Hoppe-Seyler,* 370:101–108, (1989).

Walker et al, *Cellular Immunology,* 119:470–475, (1989).

Root-Berstein, *Genetic Engineering News,* Sep. 1, 1992, pp. 4–6.

Root-Berstein, *Genetic Engineering News,* Sep. 15, 1992, pp. 4–5.

Staal et al, "Glutathione Deficiency And Human Immunodeficiency Virus Infection," *Lancet,* 339:909–912, (1992).

Staal et al, "Intracellular Glutathione Levels In T Cell Subsets Decrease In HIV-Infected Individuals," *Aids Research And Human Retroviruses,* 8(2):305–311, (1992).

Roedere et al, "N-Acetylcysteine: A New Approach To Anti-HIV Therapy," *Aids Research And Human Retroviruses,* 8(2):209–217, (1992).

Staal et al, "Intracellular Thiols Regulate Activation Of Nuclear Factor κB and Transcription Of Human Immunodeficiency Virus," *Proc. Natl. Acad. Sci. USA,* 87:9943–9947, (1990).

Roedere et al, "Cytokine-Stimulated Human Immunodeficiency Virus Replication Is Inhibited by N-acetyl-L-cysteine," *Proc. Natl. Acad. Sci. USA,* 87:4884–4888, (1990).

Roedere et al, "N-Acetylcysteine Inhibits Latent HIV Expression In Chronically Infected Cells," *Aids Research And Human Retroviruses,* 7(6):563–567, (1991).

Roederer et al, "The Interrelationship Of TNF, Glutathione, And AIDS," *TNF3* (Bassel. Karger, in press pp. 1–15, (1991).

Staal et al, "Glutathione And Immunophenotypes Of T And B Lymphocytes In HIV-Infected Individuals," *Annals N.Y. Acad. Sci.,* pp. 1–10, (1992).

Roederer et al, "CD4 And CD8 T Cells With High Intracellular Glutathione Levels Are Selectively Lost As The HIV Infection Progresses," *Intl. Immunol.,* 3(9):933–937, (1991).

Staal et al, "CD20 Expression Is Increased On B Lymphocytes From HIV-Infected Individuals," (in press), pp. 1–21.

De Quay et al, "Glutathione Depletion In HIV-Infected Patients: Role Of Cysteine Deficiency And Effect Of Oral N-Acetylcysteine," (in press), pp. 1–20.

Roedere et al, "Disregulation Of Leukocyte Glutathione in AIDS," (in press), pp. 1–23.

B. DeJong et al "Augmentation of Chinese Hamster Lymphocyte Stimulation by Cysteine" Jour. of Imm. Methods, 68 (1984) 55–60.

Ohmori et al "Mechanism of Augmentation of the Antibody Response etc." J. Exp. Med, vol. 155, May 1982, pp. 1277–1290.

Miller et al "Clinical Safety of High Oral Doses of Acetylcysteine" Seminars in Oncology, vol. 10, No. 1, Suppl. 1 (Mar.) 1983, 76–85.

Kalebic et al., Proc. Natl. Acad Sci, vol. 88 pp. 986–990, Feb. 1991 "Suppression of Human Immunodeficiency Virus Expression in Chronically etc."

Buhl et al "Systemic Glutathione Deficiency in Symptom–Free etc." The Lancet, Dec. 2, 1989, 1294–1298.

Zimmerman et al. "The Role of Oxidant Injury in Tumor Cell Sensitivity etc." The Journal of Immunology, vol. 142, 1405–1409 Feb. 15, 1989.

Fidelus et al. "Modulation of Intracellular Glutathione Concentrations etc." Experimental Cell Research 170 (1987) pp. 269–275.

Fidelus et al. "Glutathione and Lymphocyte Activation: etc." Immunology, 1987 61, pp. 503–508.

Fidelus et al. "Enhancement of Intracellular Glutathione Promotes etc." Cellular Immunology 97, 155–163 (1986).

Mitsuya et al "3'-Azido-3'-deoxythymidine etc." Proc. Natl. Acad. Sci. vol. 82, pp. 7096–7100, Oct. 1985.

METHOD OF TREATING THE SYMPTOMS OF HUMAN RHINOVIRUS INFECTION

This application is a continuation of application Ser. No. 08/159,945, filed on Nov. 29, 1993, now abandoned, which is a continuation of application Ser. No. 08/034,641, filed on Mar. 22, 1993, now abandoned, which is a continuation of application Ser. No. 07/832,606, filed on Feb. 12, 1992, now abandoned, which is a continuation-in-part of application Ser. No. 07/463,618, filed on Jan. 11, 1990, now abandoned.

BACKGROUND OF THE INVENTION

The present invention relates to a method of treating viral infection wherein the transcription or translation of viral genes or the replication of the virus is inhibited by administering an N-acylcysteine to restore thiol balance.

It is known that HIV-infected individuals have low levels of serum acid-soluble thiols and low levels of intracellular glutathione (GSH) in peripheral blood mononuclear cells (PBMC) [Eck et al., Biol. Chem. Hoppe-Seyler, 370:101–108, 1989]. Asymptomatic HIV-seropositive patients have dramatically reduced GSH levels in lung epithelial lining fluid and in blood plasma [Buhl et al., Lancet, ii:1294–1298, 1989]. Tumor necrosis factor (TNF-α) stimulates HIV transcription and viral protein production in vitro by activating the DNA binding protein NFγB which in turn increases the promoter activity of the HIV long terminal repeat and thereby increases HIV mRNA and protein levels.

TNF-α levels are abnormally high in serum samples from AIDS patients and rise as opportunistic infections become more frequent in patients with ARC and AIDS. Some of the toxic effects of TNF-α are exerted by stimulation of an intracellular oxidative (respiratory) burst which generates reactive oxidative intermediates (ROI's). Phorbol 12-myristate 13-acetate (PMA) mimics the oxidant stimulating action of TNF-α. Intracellular oxidants/ROI's are scavenged by intracellular GSH, but high levels of oxidants or depressed levels of GSH result in vulnerability to cytotoxic effects.

In a related, copending application, U.S. Ser. No. 07/459,997 (pending), filed Jan. 5, 1990, and its predecessor applications, the therapeutic effect of N-acylcysteines for HIV-infected patients is disclosed, including its antiviral effects. A need continues to exist for a general method for antiviral therapy and inhibition of expression of viral genetic material.

OBJECTS OF THE INVENTION

One object of the present invention is to provide a method for treating viral infections that prevents the onset of symptomatology.

Another object of the invention is to inhibit the spread of a viral infection by preventing viral replication.

Upon further study of the specification and appended claims, further objects and advantages of this invention will become apparent to those skilled in the art.

SUMMARY OF THE INVENTION

The foregoing objects are achieved by providing a method of treating a viral infection, comprising the step of administering to a patient harboring a disease-inducing virus other than HIV-1, said virus being one for which an intracellular thiol deficit causes or exacerbates expression of viral genetic information by transcription, translation or viral replication, an amount effective to inhibit transcriptional or translational expression of genetic information or replication of said virus, of an N-$(C_{1-4})$-acylcysteine or a pharmaceutically acceptable salt thereof. Combination of N-$(C_{1-4})$-acylcysteine or its salt with another antiviral drug or drug for alleviating symptoms of viral infection provides additional therapeutic benefits.

DETAILED DISCUSSION

It has now been found that N-$(C_{1-4})$acylcysteines and their salts (hereinafter, "NAC compounds"), especially N-acetylcysteine (NAC), are effective drugs for antiviral therapy. They are safe, non-toxic and well tolerated, especially in oral administration, and they significantly enhance the antioxidant buffering capacity of cells and directly inhibit processes which are essential for transcription and translation of viral genetic information and viral replication.

NAC counteracts the stimulatory effects of TNF-α or PMA on HIV-1 transcription, translation and replication and prevents the TNF-α-induced drop in intracellular GSH. This is a general phenomenon and recognition of the role of the intracellular thiol levels in regulation of viral gene expression enables a rational approach to therapy.

It will be appreciated that the complete viral life cycle is a result of transcription and other events, including RNA or DNA splicing and packaging, protein synthesis, viral assembly and budding, and subsequent infection. Surprisingly and unexpectedly, NAC compounds inhibit both transcriptional and translational expression of viral genetic material and viral replication, and remarkably are capable of inhibiting the stimulation of these processes by a variety of agents.

Stimulation of viral replication can occur synergistically by the combined action of two or more agents. This may be responsible for the progression of asymptomatic viral infections such as HIV-1 from latency to symptomatic stages. NAC compounds inhibit this synergy as well as the individual stimulatory actions of the agents and are therefore useful for repressing the development of symptoms in infected, asymptomatic patients similar to seropositive AIDS patients.

Virtually all viral infections are susceptible to treatment by NAC compounds. Those viruses which use transcription factors such as NFκB can be identified by recognition of regulatory sequences having κB sites on the sequence map of the virus. They will be susceptible to NAC-induced inhibition of NFκB activation and resultant inhibition of transcription of the viral genes. Other binding sites for viral transcription factors can be similarly identified.

Alternatively, the effect upon virus-infected cells in culture of oxidant inducers and NAC compounds can be tested. Those viruses which proliferate in cells that are stimulated by oxidant inducers, e.g., TNF-α and PMA, and whose proliferation is inhibited by NAC compounds, meet the criteria for susceptibility to the antiproliferative action of NAC compounds.

Infective retroviruses other than HIV-1 include, e.g., human T-cell leukemia virus (HTLV) and the like. Other infective, but non-retrovirus, RNA viruses include, e.g., rhinovirus, picornavirus, paramyxovirus, influenza virus and the like. Infective DNA viruses include, e.g., herpes virus, pox virus, papovavirus, adenovirus, parvovirus and the like.

The treatment of the patient may be with NAC or physiologically acceptable related compounds, i.e., N-acylcysteines with $C_1$–$C_4$ acyl groups, and salts of the foregoing.

Such salts include salts with pharmacologically acceptable cations including, e.g., alkaline or alkaline-earth metals, specifically sodium, potassium or calcium, or salts with physiologically acceptable bases, e.g., simple amines such as ammonia, and in particular with basic amino acids such as lysine, arginine and the like. Preferred compounds are NAC and its salts.

NAC compounds may be formulated in a variety of ways. These include but are not limited to: solid forms, such as powders, granulates, tablets, capsules, dragees; liquid forms such as sterile injectable solutions, solutions or suspensions for oral administration; suppositories; aerosols; and topical or ingestible slow-release formulations. The formulations may include conventional additives, such as flavoring, excipients, stabilizers, effervescent agents, antioxidants, or the like. These additives will be used in conventional amounts and, with the exception of excipients, will usually be present in a total amount of less than about 10 wt. %. For slow release particles, various physiologically acceptable biologically degradable polymers may be employed, such as polylactates, polyglycolates, polyaldehydes, polyanhydrides, and the like.

Liposomes may also be employed as carriers, wherein a NAC compound is present in the lumen of the liposome. Preparation of liposomes is conventional and is extensively described in the literature, and need not be described here. The concentration of the NAC compound in the liposome lumen will generally be in the range of about 50 μg/ml to 5 mg/ml. The particle size of the liposomes will generally be in the range of about 1 to 500 micron. A further improvement in delivery of the therapeutic agent can be achieved, for those diseases where the infection is associated with a specific type of cell or tissue, by conjugating to the liposomes molecules which provide for specific targeting. For example, antibodies may be bound to the liposome, either covalently or non-covalently, where the antibodies may be specific for antigens found on, in or associated with such cells or tissues, and preferably not found on healthy tissues.

Any convenient mode of administration of the NAC compounds may be employed. Administration may be oral, parenteral, topical, or the like, such as by injection, oral tablet or powder solutions or suspensions or other convenient means. Oral administration is preferred. Administration may be daily, multiple dosages per day, bidaily, or other convenient period, the dosage being dependant, in a manner well known to the clinician, upon the mode of administration, whether NAC compounds are administered in a long acting form, or the like.

The drug may be administered up to the maximum allowable dosage to provide for repression of viral transcription or proliferation and for counteracting the symptoms of viral infection. Where oral ingestion is employed, tablets, capsules (including coated or enteral tablets or capsules), granulates, powders or effervescent tablets, having about 100 mg to 1 g or more of NAC compound, may be used. The tablets and capsules are generally administered as such, while the granulates, powders or effervescent tablets are usually administered dissolved or suspended in water.

The amount of NAC compound administered to the patient per day will generally be in the range of about 200 mg to 20 g, preferably about 600 mg to 5 g, more preferably about 1 to 4 g. The foregoing level of administration is generally not associated with any significant adverse side effects and will be appropriate for maintaining and/or restoring a normal intracellular glutathione level in an asymptomatic infected patient or a patient suffering virus-induced pathology. It will be appreciated that the dosage regimen must be tailored to the particulars of the patient's condition, response and associated treatments in a manner which is conventional for any therapy, and may need to be adjusted in response to changes in condition and/or in light of other clinical indications.

The NAC and related compounds may be used in conjunction with other antiviral drugs, e.g., drugs that affect the pathogenesis of virus-induced diseases, in particular, drugs such as zinovudine (AZT) or dideoxyinosine (ddI) and the like. NAC compounds can also be used with drugs that alleviate symptoms of viral infection, e.g., antihistamines, decongestants, antitussives and the like. Finally, NAC compounds can be used with immunomodulators or cytokines, e.g., γ-interferon (INF-γ) that lower intracellular GSH levels. In each case, the NAC compounds enhance the efficacy of those drugs, either by providing another mechanism for inhibiting transcription or translation of viral genetic material or viral replication, or by counteracting or mitigating the side effects of an antiviral or symptom-relieving drug by raising intracellular GSH levels depressed by the drug's action.

The administered dosage of these drugs will vary, depending upon the disease status of the individual. Usually, antiviral drugs will be administered at a rate of about 5 μg to 100 mg/kg/d. Other drugs will be administered according to known protocols or by careful adjustment of dosage in response to symptoms.

A pharmaceutical preparation for treatment of patients suffering from viral infection, for use in the foregoing method, advantageously includes an N-($C_{1-4}$-acyl)cysteine or a pharmacologically acceptable salt thereof, in an amount of from about 100 mg to about 10 g, and at least one additional drug which affects the pathogenesis of the viral infection or which treats symptoms of the infection.

Thus, NAC compounds can palliate the symptoms of disease in patients suffering from viral infections, including those considered to be refractory to chemotherapy, and improve the quality of their lives. They can also help to prevent or delay the onset of clinical symptoms in patients with latent viral infections. In addition, they are useful for adjunctive therapy with other antiviral or symptom-relieving drugs.

The following examples are offered by way of illustration and not by way of limitation.

EXAMPLE 1

A female patient who suffers frequent acute symptoms due to herpes simplex virus infection is given 1–2 doses of 200 mg N-acetyl cysteine every day for a period of two years. NAC is administered by drinking a water solution/ suspension of a commercially available granulate. No further symptoms appear during the test period, showing that latency is maintained by the NAC treatment. Within four weeks of discontinuation of NAC therapy, acute symptoms reappear.

EXAMPLE 2

A group of 40 healthy male volunteers is divided into four well-paired groups of ten volunteers each. The first group is given five 200 mg oral doses of NAC per day for one week. At the end of the week, all volunteers are exposed to an infective dose of rhinovirus. The first group continues to receive five 200 mg oral doses of NAC per day for three more weeks. The second group is given five 200 mg oral doses of NAC per day for three weeks, starting with the day of viral infection. The third group is given five 200 mg oral doses of NAC per day starting with the fourth day after viral infection and ending three weeks post-infection, while the fourth group receives no NAC. All four groups are observed for a period of three weeks following exposure to the virus.

The first group shows no acute cold symptoms during the three-week trial period. The second group shows only mild symptoms, including low fever, headaches, some nasal congestion and mild throat irritation. The third group develops more acute symptoms starting three days post-infection, which moderate significantly within 1–3 days after beginning NAC therapy. The fourth group develops acute cold symptoms within three days post-infection that persist for 1–2 weeks.

These results show that NAC can prevent the onset of cold symptoms if administered prior to viral infection and can significantly inhibit and ameliorate the development of symptoms if administered concurrently or soon after exposure to the virus.

Further investigation shows that administration of 2–5 200 mg oral doses per day of NAC to a patient suffering from symptoms resulting from rhinovirus infection and also taking a commercial cold relief medicine provides additional relief and accelerated recovery.

It is evident from the above results that the administration of NAC compounds can serve to substantially reduce the severity of symptoms resulting from viral infections. NAC compounds also repress viral gene transcription and translation and viral replication and therefore inhibit both the spread of viral genetic material and viral proliferation that results in the onset of symptoms. Together with other antiviral drugs or drugs for alleviation of symptoms of viral infection, NAC compounds provide additional therapeutic benefits and can counteract deleterious side effects of the other drugs.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the invention, as defined by the appended claims.

What is claimed is:

1. A method of treating symptoms of human rhinovirus infection, comprising the step of orally or parenterally administering to a patient in need thereof, an effective amount of an $N\text{-}(C_{1\text{-}4})$-acylcysteine or a pharmaceutically acceptable salt thereof, wherein said $N\text{-}(C_{1\text{-}4})$-acylcysteine or pharmaceutically acceptable salt thereof is administered in an amount of from about 600 mg to 5 g per day.

2. A method of treating symptoms of human rhinovirus infection, comprising the step of orally or parenterally administering to a patient in need thereof an effective amount of N-acetyl cysteine or a pharmaceutically acceptable salt thereof, wherein said N-acetyl cysteine or pharmaceutically acceptable salt thereof is administered in an amount of from about 600 mg to 5 g per day.

* * * * *